United States Patent
DiFoggio et al.

(10) Patent No.: US 9,733,182 B2
(45) Date of Patent: Aug. 15, 2017

(54) APPARATUS AND METHOD FOR DETERMINING A FLUID PROPERTY DOWNHOLE USING A BULK READING REFRACTOMETER

(71) Applicants: Rocco DiFoggio, Houston, TX (US); Thomas Kruspe, Niedersachsen (DE); Sebastian Jung, Lower Saxony (DE)

(72) Inventors: Rocco DiFoggio, Houston, TX (US); Thomas Kruspe, Niedersachsen (DE); Sebastian Jung, Lower Saxony (DE)

(73) Assignee: BAKER HUGHES INCORPORATED, Houston, TX (US)

( * ) Notice: Subject to any disclaimer, the term of this patent is extended or adjusted under 35 U.S.C. 154(b) by 0 days.

(21) Appl. No.: 13/856,815

(22) Filed: Apr. 4, 2013

(65) Prior Publication Data
US 2014/0300889 A1  Oct. 9, 2014

(51) Int. Cl.
*G01V 8/10* (2006.01)
*G01N 21/41* (2006.01)
(Continued)

(52) U.S. Cl.
CPC ......... *G01N 21/4133* (2013.01); *E21B 47/10* (2013.01); *G01N 33/2823* (2013.01);
(Continued)

(58) Field of Classification Search
CPC ... G01V 8/10; G01V 8/20; G01V 8/12; G01N 21/4133; G01N 30/74; G01N 21/05;
(Continued)

(56) References Cited

U.S. PATENT DOCUMENTS 4,641,965 A * 2/1987 Harmer .................. 356/135
5,167,149 A  12/1992 Mullins et al.
(Continued)

FOREIGN PATENT DOCUMENTS

BE     EP 2543839 A1 *  1/2013  ............. F01N 11/00
DE  WO 2008107336 A1 *  9/2008  ............. G01N 21/43
(Continued)

OTHER PUBLICATIONS http://www.newport.com/How-to-Clean-Optics/141176/1033/content.aspx.*
(Continued)

*Primary Examiner* — Tarifur Chowdhury
*Assistant Examiner* — Mohamed K Amara
(74) *Attorney, Agent, or Firm* — Cantor Colburn LLP

(57) ABSTRACT

In one aspect, an apparatus for determining a property of a fluid is disclosed that in one embodiment may include a transparent member having an axis and a first end substantially perpendicular to the axis and a second end having an outer surface at a first angle to the axis, a light source directing light at the first end, a detector placed spaced from the second end, the space between the second end and the detector containing a fluid, wherein the detector detects light exiting from the outer surface at a second angle to the axis and passing through the fluid, and a controller for determining the second angle from the light detected by the detector. A processor determines the bulk fluid refractive index from the light detected by the detector and a property of the fluid therefrom.

24 Claims, 3 Drawing Sheets

(51) Int. Cl.
  *G01N 33/28* (2006.01)
  *E21B 47/10* (2012.01)
  *E21B 49/08* (2006.01)
  *G01N 21/43* (2006.01)

(52) U.S. Cl.
  CPC .. *E21B 2049/085* (2013.01); *G01N 2021/434* (2013.01); *G01N 2021/437* (2013.01)

(58) Field of Classification Search
  CPC ............... G01N 30/78; G01N 21/41; G01N 2021/4153; G01N 21/431; G01S 17/42; G01P 3/68
  USPC ......... 356/128, 130, 246, 135, 131, 132, 51, 356/302, 343, 300
  IPC .......................................................... G01P 3/68
  See application file for complete search history.

(56) References Cited

U.S. PATENT DOCUMENTS

| | | | |
|---|---|---|---|
| 5,201,220 A | | 4/1993 | Mullins et al. |
| 5,210,404 A | * | 5/1993 | Cush ................. G01N 21/7743 250/216 |
| 5,696,580 A | * | 12/1997 | Kubo et al. ..................... 356/72 |
| 6,172,746 B1 | | 1/2001 | Byrne et al. |
| 6,683,681 B2 | | 1/2004 | DiFoggio et al. |
| 6,731,380 B2 | * | 5/2004 | Amara et al. .................. 356/73 |
| 6,842,256 B2 | | 1/2005 | Hill |
| 6,997,055 B2 | | 2/2006 | DiFoggio |
| 7,016,026 B2 | | 3/2006 | DiFoggio et al. |
| 7,061,597 B2 | * | 6/2006 | Oberleitner et al. ......... 356/135 |
| 7,637,151 B2 | | 12/2009 | Raghuraman et al. |
| 7,788,972 B2 | | 9/2010 | Terabayashi et al. |
| 7,852,468 B2 | | 12/2010 | DiFoggio |
| 8,109,157 B2 | | 2/2012 | Kanayama et al. |
| 2003/0095248 A1 | * | 5/2003 | Frot ..................... G01N 21/431 356/128 |
| 2004/0109156 A1 | | 6/2004 | DiFoggio et al. |
| 2004/0130706 A1 | * | 7/2004 | Frot .............................. 356/128 |
| 2005/0110989 A1 | * | 5/2005 | Schermer ............. G01N 21/253 356/246 |
| 2009/0103085 A1 | * | 4/2009 | Hu ......................... G01N 21/41 356/320 |
| 2009/0122300 A1 | * | 5/2009 | Wu ..................... G01N 21/4133 356/128 |
| 2009/0279074 A1 | * | 11/2009 | Seaver ............... G01N 21/4133 356/73 |
| 2011/0188030 A1 | * | 8/2011 | Verschuren ........... G01N 21/41 356/128 |
| 2011/0203386 A1 | | 8/2011 | Johansen |
| 2012/0081698 A1 | * | 4/2012 | Christian et al. ............. 356/128 |
| 2013/0214138 A1 | * | 8/2013 | Chiarello ............. G01N 21/431 250/227.11 |
| 2014/0132951 A1 | * | 5/2014 | Georis .................... F01N 11/00 356/72 |
| 2014/0300889 A1 | * | 10/2014 | DiFoggio ........... G01N 21/4133 356/51 |
| 2016/0018326 A1 | * | 1/2016 | Jeanotte ................. G01N 21/05 356/130 |

FOREIGN PATENT DOCUMENTS

| | | | | |
|---|---|---|---|---|
| JP | 2005257319 A | * | 9/2005 | ............. G01N 21/59 |
| WO | WO 9802730 A1 | * | 1/1998 | ............. G01N 21/41 |

OTHER PUBLICATIONS

PCT International Search Report and Written Opinion; International Application No. PCT/US2014/032630; International Filing Date: Apr. 2, 2014; Date of Mailing: Jul. 28, 2014; pp. 1-10.

* cited by examiner

APPARATUS AND METHOD FOR DETERMINING A FLUID PROPERTY DOWNHOLE USING A BULK READING REFRACTOMETER

BACKGROUND OF THE DISCLOSURE

1. Field of the Disclosure

The present disclosure relates generally to apparatus and methods for determining a refractive index of a fluid and one or more properties or characteristics of the fluid therefrom, such as fluid recovered from subsurface formations.

2. Description of the Related Art

During both drilling of a wellbore and after drilling, fluid (oil, gas and water) from the formation is often extracted to determine the nature of the hydrocarbons in hydrocarbon-bearing formations. Fluid samples are often collected in sample chambers and the collected samples are tested to determine various properties of the extracted formation fluid. To drill a well, drilling fluid is circulated under pressure greater than the pressure of the formation in which the well is drilled. The drilling fluid invades or penetrates into the formation surrounding the wellbore to varying depths, referred to as the invaded zone. The drilling fluid contaminates the original (virgin) fluid present in the invaded zone. To collect samples of the original fluid present in the formation, a formation testing tool is often conveyed into the wellbore. A pump typically extracts the fluid from the formation via a sealed probe placed against the inside wall of the wellbore. A fluid identification device is typically utilized to determine the contamination level in the fluid. When the fluid is initially extracted, it contains high amounts of the drilling fluid filtrate. The extracted fluid is typically discarded into the wellbore until the fluid identification device measurements indicate that an acceptably low level of contamination has been achieved. Refractometers have been utilized to determine or infer the contamination level in the formation fluids during extraction. Current downhole refractometers are typically based on measurements related to the reflection of light at a window-fluid interface, such as the critical angle of reflection or the intensity of the reflection (at near-normal incidence). Such refractometers are primarily sensitive to the interface region between the fluid and a transparent window (often sapphire) immersed in the fluid, which interface region is only few microns (wavelengths of light) of the fluid beyond the refractometer window that is immersed in the fluid of interest. Often, the refractometer window accumulates a thin film of deposits from the formation fluid. The refractive index measurements then become less reliable because they, at least in part, depend upon the refractive index of this film, and, if the film is thick enough, they only depend on the refractive index of the film.

The disclosure herein provides a refractometer that is substantially unaffected by certain deposits on the window and may be more reliably utilized in downhole tools for determining characteristics of a formation fluid.

SUMMARY

In one aspect, an apparatus for determining a property of a fluid is disclosed that in one embodiment may include a transparent window member having an axis and a first end substantially perpendicular to the axis and a second end having an outer surface at a first angle with respect to that axis, a light source directing light at the first end, a detector placed a selected distance beyond the transparent window member from the second end, the space between the second end and the detector containing a fluid, wherein the detector detects the location at which a beam of light exiting from the outer surface at a second angle to the axis and transmitted through the fluid strikes the detector, and a controller for determining the second angle from the location where this light strikes the detector. A processor determines the bulk fluid refractive index from the light detected by the detector and a property of the fluid therefrom.

In another aspect, the apparatus includes a first refractometer for determining a bulk fluid refractive index of a fluid from a light transmitted through a selected fluid and a second refractometer for determining a refractive index of the interface-region fluid based on a reflection of the light from the fluid-window interface. A processor may determine a quality level of one of the determined refractive indices relative to the other and also may determine one or more properties of the selected fluid from one or both of the determined indices.

Examples of certain features of the apparatus and methods disclosed herein are summarized rather broadly in order that the detailed description thereof that follows may be better understood. There are, of course, additional features of the apparatus and methods disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, wherein.

DESCRIPTION OF THE FIGURES

Figure 1:
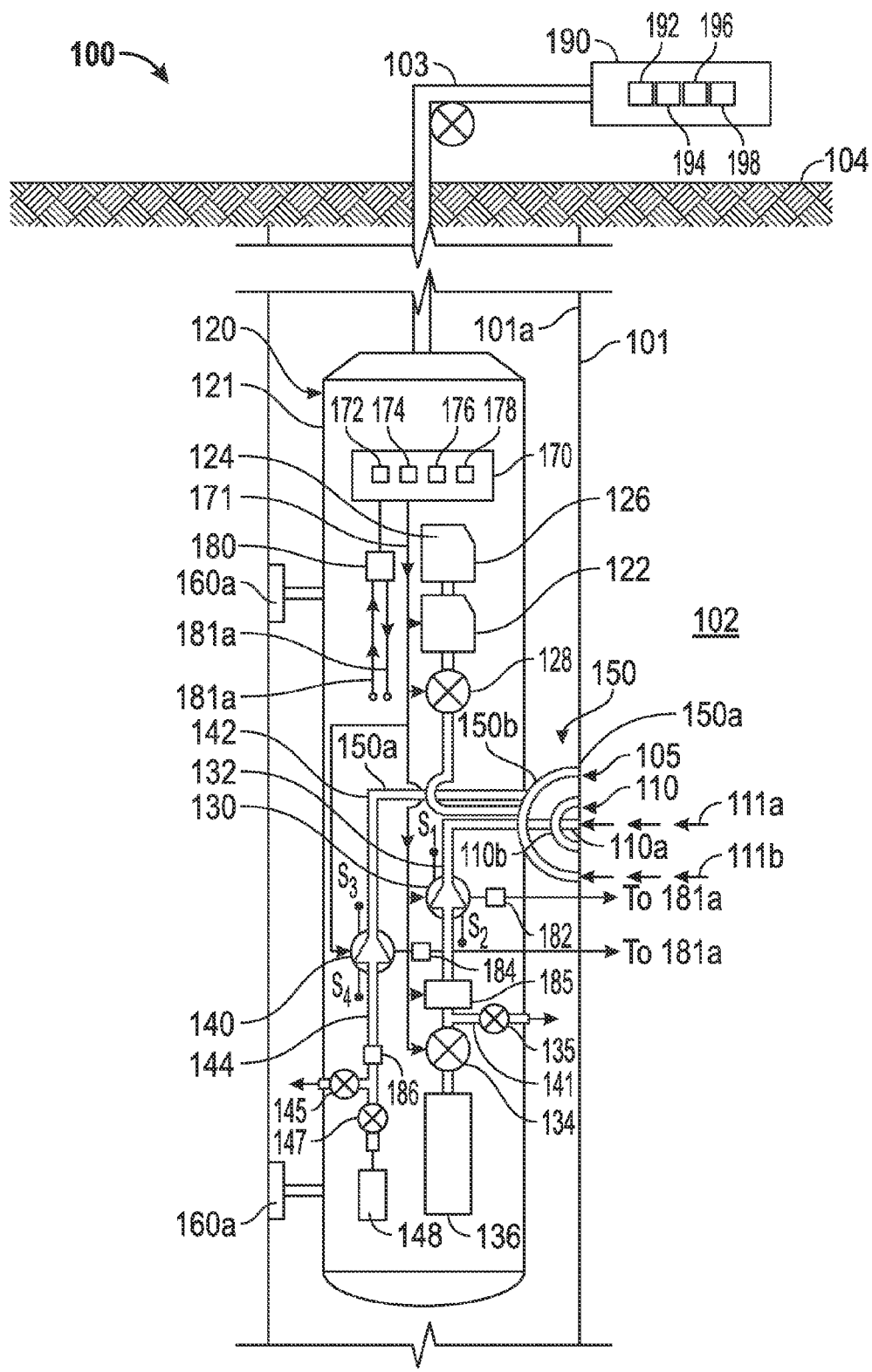
FIG. 1 is a schematic diagram of an exemplary formation testing system for obtaining formation fluid samples that utilizes a refractometer for determining a characteristic or property of interest of the formation fluid, according to one embodiment of the disclosure.

FIG. 1 is a schematic diagram of an exemplary formation evaluation system 100 for obtaining formation fluid samples and retrieving such samples for determining one or more properties of such fluid. The system 100 is shown to include a downhole formation evaluation tool 120 deployed in a wellbore 101 formed in a formation 102. The tool 120 may be conveyed into the wellbore 101 from the surface 104 by any suitable conveying member 103, such as a wireline, a coiled tubing, a drilling tubular, etc. In one embodiment, the tool 120 includes a fluid extraction or fluid withdrawal device 105 that includes an inner probe 110 and an outer probe 150. In one embodiment, probes 110 and 150 are concentric, as shown in FIG. 1. Probe 110 includes a fluid conduit or line 110a and a seal 110b, such as a pad or packer, around the conduit 110a. The outer probe 150 includes a conduit or fluid line 150a and a seal 150b around the conduit 150a. In one configuration, probes 110 and 150 may be extended from a tool body 121 radially outward toward the wellbore wall 101a. A pump 122 supplies a fluid 124 under pressure from a fluid chamber 126 to probes 110 and 150 via a fluid line 127 to extend and urge probes 110 and 150 against the inside wall 101a of the wellbore 101. Pads 160a and 160b on the opposite side of the fluid withdrawal device 105 are extended so that the probes 110 and 150, when extended, will urge against the wellbore wall 101a. A flow control device 128, such as a valve, associated with or in line 127, may be provided to control the flow of the fluid 124 to the probes 110 and 150.

A pump 130 is coupled to the inner probe 110 via a fluid line 132 for withdrawing fluid 111a from formation 102 via line 110a. To draw or extract fluid 111a from formation 102, pump 130 is activated, which extracts the fluid 111a into line 110a. The extracted fluid may be pumped into a chamber 136 via a flow control device 134 or discharged into the wellbore 101 via a fluid line 141 and the flow control device 134. A pump 140 is coupled to the outer probe 150 via a fluid line 142 for withdrawing fluid 111b from formation 102 via line 150a. To draw or extract fluid 111b from formation 102, pump 140 is activated to extract the fluid 111b into line 150a and thus line 142. The fluid withdrawn into line 142 may be discharged into the wellbore 101 via a line 144 and valve 145 or into a collection chamber 148 via line 146 and valve 147.

The tool 120 further includes a controller 170 that contains circuits 172 for use in operating various components of the tool 120, a processor 174, such as a microprocessor, a data storage device 176, such as a solid state memory, and programs 178 accessible to the processor 174 for executing instruction contained therein. The system 100 also includes a controller 190 at the surface that contains circuits 192, a processor 194, a data storage device 196 and programs 198 accessible to processor for executing instructions contained therein. Controllers 170 and 190 are in a two-way communication with each other and either alone or in combination may control the operation of the various devices in tool 120.

To obtain clean formation fluid samples, the tool 120 is conveyed and placed at a selected depth in the wellbore 101. Pads 160a and 160b are activated to contact the wellbore wall 101a. The inner probe 110 and outer probe 150 are activated to urge against the wellbore wall 101a to seal the probes 110 and 150 against the wellbore wall 101a. In one aspect, both the inner and outer probes 110 and 150 are activated simultaneously or substantially simultaneously. Pumps 130 and 140 are activated to draw the formation fluid into their respective probes. Activating pump 140 causes the fluid 111b around the probe 110 to flow into the outer probe 150, while activating pump 130 causes the fluid 111a to flow into the inner probe 110. The fluid initially drawn through the probes 110 and 150 (111a and 111b) is the fluid present in the invaded zone and is thus contaminated. A fluid evaluation or testing device 185 may be used to determine when the fluid 111a being withdrawn from probe 110 is sufficiently clean so that fluid samples may be collected. Similarly, a fluid evaluation device 186 may be utilized to determination the contamination level of the fluid 111b withdrawn from probe 150. Any device, including, but not limited to, an optical device, may be utilized for determining contamination in the withdrawn fluids. As long as the contamination in the fluid 111a being withdrawn from probe 110 is above a threshold or is otherwise not satisfactory, such fluid may be discharged into the wellbore 101 via a flow control device 135 and fluid line 141. Once the fluid 111a is clean (e. e., below a threshold), the fluid may be collected in sample chamber 136 by opening valve 134 and closing valve 135, The pump 140 continues to pump the fluid 111b from the probe 150 into the wellbore 101 or into chamber 148. The pumps and flow control devices in the tool 120 may be controlled by the controller 170 according to instructions stored in programs 178 and/or instructions provided by the surface controller 190. Alternatively, controller 190 may control the operation of one or more devices in the tool 120 according to instructions provided by programs 198.

Still referring to FIG. 1, in one embodiment, various devices in the tool 120, such as pumps 130 and 140, are hydraulically-operated devices and are controlled using a common hydraulic power unit 180 and a common or single hydraulic line 181a and a return line 181b. The hydraulic power unit 180 supplies a hydraulic fluid 180a under pressure to the common hydraulic line 181a, which fluid returns to the power unit 180 via the return line 181b. A variable flow control device 182 between the hydraulic line 181a and the pump 130 controls the supply of the hydraulic fluid 180c to pump 130, which controls the operation (for example speed) of the pump 130. Similarly, a variable flow control device 184 between the hydraulic line 181a and pump 140 controls the speed of the pump 140. Sensors S1 and S2 provide signals indicating end of the stroke in either direction of pump 130, while sensors S3 and S4 provide signals indicating end of the stroke in either direction of pump 140. Any suitable sensor, including, but not limited to, a magnetic switch and a Hall effect sensor, may be utilized for the purpose of this disclosure. Controllers 170 and/or 190 may be utilized to control the variable flow control devices 182 and 184 to independently control the pumps 130 and 140 and any other device in hydraulic communication with the hydraulic line 181a and to control starting and stopping of pumps 130 and 140 utilizing the signals provided by sensors S1, S2, S3 and S4.

Figure 2:
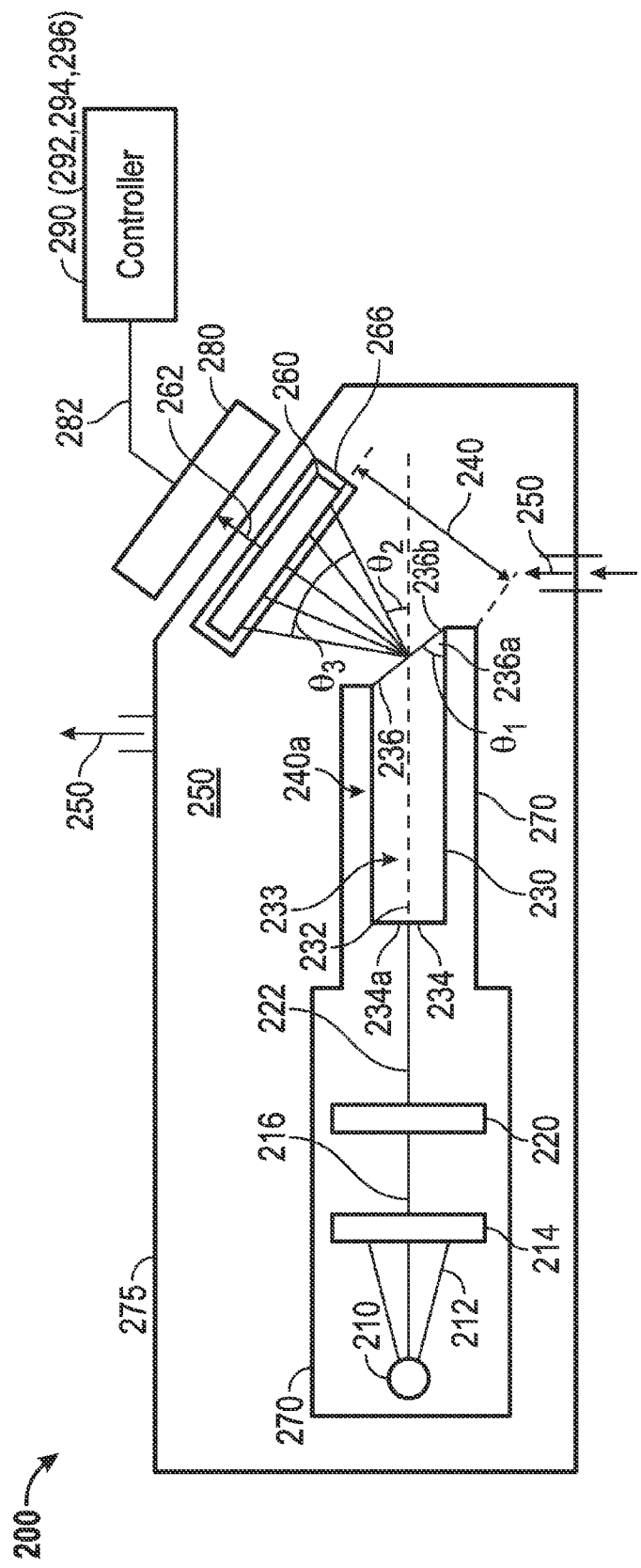
FIG. 2 is schematic diagram of a refractometer for determining a bulk fluid refractive index and for determining a characteristic or property of interest of a fluid therefrom, according to one embodiment of the disclosure.
Figure 3:
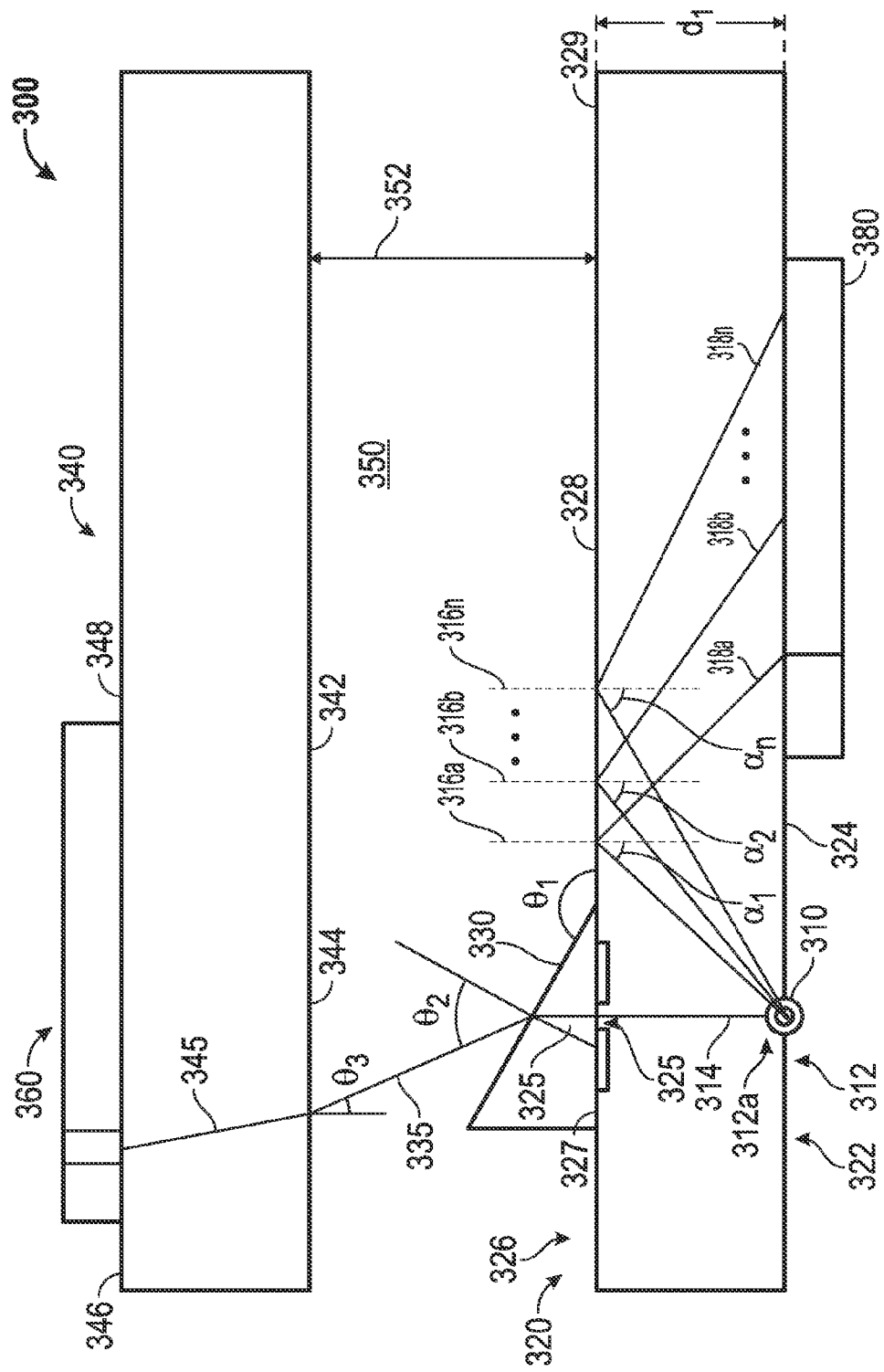
FIG. 3 is a schematic diagram of a device for determining a bulk fluid refractive index from the angle of transmission of light exiting a surface and transmitted through a bulk fluid and an interface-fluid refractive index from reflection of light from a fluid interface, according to another embodiment of the disclosure.

As noted above, fluid identification devices 185 and 186 respectively mat be utilized for determining one or more characteristics of the formation fluid. In one aspect, the tool 120 may utilize a refractometer for determining the characteristics of the fluid downhole. FIGS. 2 and 3 describe exemplary refractometers that may be utilized in tool 120 for determining the characteristics of the fluids 111a and 111b. FIG. 2 is a schematic diagram of a refractometer 200 for determining a bulk fluid refractive index of a fluid and for determining a property of interest of the fluid therefrom. The refractometer 200 includes a light source 210, a collimator 214, an optical bandpass light filter 220, a transparent member 230 and a detector 280. In one aspect, the transparent member may be a glass rod. The light source 210 generates a light beam 212, which is directed to the collimator 214. The light source 210 may be any suitable light source, including, but not limited to, a white light source (a wideband light source that may include visible light, infrared light or both), such as a tungsten bulb, a wideband filtered white light source that covers the wavelength range of a suitable detector array, a super luminescent diode, a light emitting diode and a laser. In one aspect, the collimator 214 provides a collimated light beam 216 along the axis of the transparent rod, 230. The optical bandpass filter 220 filters the light beam 216 and provides light beam 222 of selected wavelengths. In one aspect, one of the selected wavelengths may be the wavelength that exhibits relatively low absorbance in asphaltene from crude oil and a relatively small molecular vibrational interference from oil or water absorption peaks, such as "clear" wavelengths of 1300 nm, 1600 nm or some longer wavelengths at which asphaltenes have minimal absorbance. For longer wavelengths of the light, InGaAs (indium-gallium-arsenide) photodetectors for detecting light may be utilized, as described later. With sufficient light intensity and a sufficiently short path length, "D", a shorter wavelength of light, such as a wavelength less than 1100 nm, may be used. Less expensive and more temperature stable silicon photodetectors may be utilized with such short wavelengths. In another aspect, an imaging fiber optic bundle may be immersed in the fluid 250 to carry the images of the light that pass through the fluid 250 to a Position Sensitive Detector (PSD) or to a photodetector array located behind a pressure housing.

The light beam 222 from the filter 220 is directed to the transparent member 230. In one configuration, the transparent member 230 may have an axis 232, a first end 234 having a vertical or substantially vertical surface 234a, and a second end 236 having a surface 236a at an angle $\theta_1$ relative to the longitudinal axis 232. In one aspect, the face 236a may include a polished surface 236b. The light beam 222 is directed to the vertical face 234a of the transparent member 230. The light beam 222 travels through the transparent member 230 along an axial path 233, which path, in one aspect, may coincide with the axis 232 of the transparent member 232. The light beam 222 exits the face 236b of the transparent member 232 as a light beam 240 at an angle $\theta_2$ relative to the axis 232 of the transparent member 230. The light beam 240 passes through a fluid 250 and impinges on the detector 260. The detector 260 detects the location of light beam 240 and provides signals 262 relating to the detected light to a circuit 280. In one aspect, the circuit 280 conditions, processes and digitizes the signals 262 and provides the digitized signals 282 to a controller 290. The controller 290 determines the angle $\theta_2$ from the signals 282 and the bulk fluid refractive index of the fluid 250 therefrom and may determine a property of interest or a characteristic of the fluid 250 from the determined refractive index, n. In aspects, the property of interest may include, but is not limited to, an estimated fluid density based on correlation to the Clausius-Mossotti ratio, $(n^2-1)/(n^2+2)$, an estimated brine salinity or gas dryness based on n, or the carbon dioxide content of natural gas based on n.

Downhole refractometers typically are based on reflection critical angle measurements or reflection intensity. Such refractometers, in general, provide optical measurements of an interface-fluid that is only a few microns of fluid beyond the refractometer window immersed in the fluid. If the refractometer window is not perfectly or near perfectly clean but has a thin film of deposits from the formation fluid, then optical measurements for such deposits will be erroneously included in the measurement of the refractive index of the fluid. The above described apparatus 200 and methods measure a bulk-reading rather than the measurements relating to the interface fluid as performed by the current downhole refractometers. In the apparatus of FIG. 2, the light 240 travels at least a distance greater than a few wavelengths of light (evanescent wave distance), such as a few millimeters, through the fluid 250, which provides measurements of the refractive index essentially unaffected or substantially unaffected by some deposits on the surface 236b of the transparent member 230. By applying Snell's law multiple times, it is known that a plate of intervening refractive index material sandwiched between two different refractive index materials does not change the final angle at which the light emerges but only introduces a lateral shift in the light beam that is less than the thickness of the plate. For a thin film "plate", the lateral shift is only a few microns and is negligible. In the embodiment of FIG. 2, very accurate measurement of the intensity of the light is not necessary to determine the location at which the center of the light beam strikes a photodetector array or a position sensitive detector (PSD). A device, such as device 200, may be utilized to accurately locate the angle at which the light 240 exits the surface 234b of the transparent member 230. Relatively accurate determination of the angle $\theta_2$ from the position of the center of the light spot on the detector 260, can provide accurate refractive index measurement. In one aspect, the angle $\theta_2$ can be relatively accurately measured with a position sensitive detector (PSD) or a photodetector array that is protectively encapsulated in a clear material 266 and immersed in the fluid 250 and placed at a fixed position relative to the polished face 236b of the transparent member 230.

Still referring to FIG. 2, in one aspect, the transparent member 230 may be a transparent rod having selected characteristics or properties. In one aspect, the refractive index of the transparent rod 230 and the face angle $\theta_2$ may be selected so as to maximize (for example up to approximately 50 degrees) the angular spread $\theta_3$ of the emitted light beam 240 angles for a desired or an expected range of fluid refractive indices. For formation fluids, one desired range may be between 1.0 for air to 1.33 for water to 1.6 for crude oil. For maximum angular spread $\theta_3$ and refractive index resolution, a relatively low refractive index rod made from a transparent material that is very insoluble and chemically resistant may be utilized. Also, the transparent rod having a refractive index within the refractive index of the desired fluid range, such 1.0 and 1.6 may be selected for better resolution and optical efficiency. In such a case, the light 240 transmitted into the fluid 250 could either be bent towards the normal or away from it depending on the fluid's refractive index relative to that of the transparent rod 230. In one embodiment, the transparent rod may be made of a commercially available chemically-resistant Schott optical glass 8330 (refractive index 1.473). Modeling shows that if the angle $\theta_2$ of the face 236b relative to the axis 232 of the transparent member 230 is 42.7 degrees, then the resultant angular spread $\theta_3$ will be of the order 48.72 degrees for light 240 transmitted through the fluid with a refractive index that ranges between 1.0-1.6. The larger the spread in angle with fluid refractive index, the more sensitive the device will be to small changes in refractive index. The cut angle and the refractive index of the rod 230 can be chosen to maximize the refractometer's sensitivity to refractive index changes. For better angular resolution, the detector array 260 may be located farther from the face 236b of the transparent rod 230. In such a case, a higher intensity light beam 212 may be utilized to compensate for the attenuation of the light through a greater distance in crude oils. Any method of relatively accurately determining the angle $\theta_2$ may be utilized, including, but not limited to, Savitzky-Golay interpolation between adjacent pixels of a photodiode array for locating the center of the light spot 240a for determining the angle $\theta_2$. From the angle $\theta_2$, the refractive index of the fluid 250 is determined and from which an estimate of a property of the fluid 250 is determined. For example, salinity of brine may be determined from the refractive index, downhole pressure, and downhole temperature.

Still referring to FIG. 2, for downhole applications, some or all elements of the refractometer 200, such as the light source 210, collimator 214, filter 220 and the transparent member 230 may be enclosed in a pressure housing, such as housing 270, with the transparent member surface 236b exposed to the fluid 250, wherein the housing seals around the transparent member 230, and prevents any fluid from leaking past it. The housing 270 may be enclosed in a chamber 275 having a fluid inlet 275a and a fluid outlet 275b. During formation testing, the fluid 250 may be withdrawn from the formation and passed through the chamber 275. The detector 260 may be placed in a protected enclosure 266 in the chamber 275. The circuit 280 and the controller 290 may be located at any suitable location in the downhole tool.

In operation, the fluid 250 passes through the device 200, the detector continuously or continually detects the light beam 240 and the controller 290 determines the angle and the refractive index of the fluid 250. In one aspect, the controller 290 includes a processor 292, such as a microprocessor, a data storage device 294, such as memory device and programs 296 containing instructions for execution by the processor 292. The controller may be located in the downhole tool, such as tool 120, FIG. 1, or at the surface or partially in the tool and partially at the surface. The refractive index of the fluid 250 and the properties of interest of such fluid may be determined in real time and utilized to take one or more samples of the formation fluid as described in reference to FIG. 1 above.

FIG. 3 is line diagram of a device 300 for use in a refractometer for determining a combination of a bulk fluid refractive index of a fluid as described in reference to FIG. 2 and for determining a refractive index using light reflection from an interface between a transparent member and the fluid. The device 300 is shown to include a first transparent member 320 that has a first side 322 with a planar surface 324. The transparent member 320 also has a second side 326 with a planar surface 328. An angular section 330 of the side 326 includes a surface 332 at a selected angle $\theta_1$. In one aspect, the face 332 may be a polished surface. In one aspect, the transparent member 320 has a thickness dl with parallel sides 322 and 326. The transparent member 320 includes an aperture 325 along an interface 327 between the angular section 330 and the planar section 326 for allowing a beam of light to pass from the source 310 to the face 332. In one aspect, the angular section 330 is a prism. The device 300 may further include a second transparent member 340 having a first planar side 342 facing the side 326 of transparent member 320 and a second side 346 opposite the first side 342. The second side 346 has a planar surface 348. In one aspect, the transparent members 320 and 340 form transparent windows of a refractometer, wherein each such window may be made from a pressure resistant glass. A fluid of interest 350, such as the formation fluid, passes between the transparent members 320 and 340 in the space 352 between the transparent members 320 and 340. In the particular embodiment of FIG. 3, the fluid 350 is in contact with the surfaces 332 and 328 of the transparent member 320 and with the surface 344 of transparent member 340.

In one aspect, a point light source 310 may be placed or attached to a selected location 312 on the transparent member 320 to direct light 312a of suitable wavelengths into the transparent member 320 at point 312. A light beam 314 is directed toward the aperture 325, which light beam passes through the angled transparent section 330 and then refracts off the surface 332 at an angle $\theta_2$ providing a light beam 335. Light beam 335 enters the transparent member 340 at an angle $\theta_3$ and impinges on the detector 360 as light beam 345. The detector 360 may be placed on or proximate the transparent member 340 to detect light 345 passing through the transparent member 340. A circuit, such as circuit 280, FIG. 1, and a controller, such as controller 290, FIG. 1, may be utilized to condition and process signals from detector 360 to determine the bulk fluid refractive index of the fluid 350. The light source 310 also directs light beams, such as light beams 316a, 316b . . . 316n, to the surface 328 of the transparent member 320. Such light beams reflect from the interface 329 between the surface 328 and fluid 350 and return as light beams 318a, 318b . . . 318n respectively to the surface 322 of the transparent member 320. The angles of reflection $\alpha_1, \alpha_2 \ldots \alpha_n$ represent angle of total reflection of light beams 216a, 216b . . . 216n. A detector 380, such as photodetector, detects the light reflected from the interface and determines therefrom the refractive index of the fluid 350. Method of determining the refractive indices from reflection light, such as light 318a, 318b . . . 318n and from the measurements from beams, such as light beam 355 passing through a fluid, are known in the art and thus not described in detail.

Thus, in an aspect, a point light source is attached to an optically transparent and pressure resistant transparent member or window. A portion of the light is directed to the fluid under an angle range, which includes the angle of total reflection. Light reflected from the fluid is detected by a first photodetector array up to the angle of total reflection. The critical angle is the angle beyond which there is total reflection and it is equal to the arcsine of the ratio of other medium's refractive index to the incident medium's refractive index based on Snell's Law $n_1 \sin \theta_1 = n_2 \sin \theta_2$, when $\theta_2$ relative to the normal to the surface equals its maximum value of 90 degrees. Therefore, the position of the light/dark shadow on the first detector array is a measure of refractive index of the fluid. A second portion of the light from the point source passes a small orifice before it enters a prism. On the interface between the prism and fluid the light beam is bent according to the Snell's Law. It passes the fluid and a second pressure resistant window before it is detected by a second photodiode array. The position of the light beam on the second photodiode array is a measure of refractive index of the fluid. A comparison of the bulk-fluid reading to the interface-fluid reading allows determination of whether the interface fluid is different than the bulk fluid because of precipitation of wax or asphaltenes on the window, bubble formation or dew condensation, which often occurs first at a solid surface such as a window, or other anomalies that result in differences between the interface fluid and the bulk fluid.

In one aspect the arrangements for determining both the bulk fluid refractive index and the refractive index from reflection as shown in FIG. 3 may be arranged as a single or common sensor arrangement. In aspects, the combination sensor provides a bulk fluid refractive index of a fluid of interest and refractive index measurement of the same. One of the refractive index measurements may be utilized to verify the other refractive index measurement. The refractive index determined from the reflection may be more accurate for fluids that are not sufficiently transparent, such as crude oils, because such fluids do not allow sufficient light to pass through the fluid for detection by the photodetector array. Also, the combination measurements allow measuring transparency of fluids and detecting surface contaminations that influence the reflection measurements. Thus, the device of FIG. 1 may be considered as having a first refractometer for determining a bulk fluid refractive index from transmission of light and a second refractometer for determining the refractive index of the fluid from reflection of light.

While the foregoing disclosure is directed to the embodiments of the disclosure, various modifications will be apparent to those skilled in the art. It is intended that all variations within the scope and spirit of the appended claims be embraced by the foregoing disclosure.

The invention claimed is:

1. An apparatus for determining a property of a downhole fluid, comprising:
   a transparent member having a first side having a planar surface, a second side having a planar surface parallel to the planar surface of the first side and an angular section of the second side having an angled surface at a selected angle to the planar surface of the first side, wherein the angled surface and the parallel surface of the second side are in contact with the downhole fluid;
   a light source at the first side that directs light through the transparent member onto the angled surface and the parallel surface of the second side;
   a first detector spaced from the second side, the space between the second side and the first detector containing the downhole fluid, wherein the first detector detects light exiting from the transparent member into the downhole fluid via the angled surface at a refractive angle;
   a second detector that receives light from the light source that is reflected by the parallel surface of the second side at a reflective angle; and
   a controller for determining the refractive index of the downhole fluid from at least one of the refractive angle at the angled surface and the reflective angle at the second surface.

2. The apparatus of claim 1, wherein the angled surface and the planar surface of the second side are polished surfaces in contact with the fluid.

3. The apparatus of claim 2, wherein the determined refractive index of the fluid is a bulk fluid refractive index.

4. The apparatus of claim 1 further comprising a filter between the light source and the transparent member that provides light having a wavelength selected from a group consisting of: a wavelength at which there is low asphaltene absorbance from crude oil and low molecular vibrational interface from oil or water; 1100 nm; 1300 nm; 1400 nm; 1600 nm; a wavelength above 1600 nm; and a wavelength below 1000 nm.

5. The apparatus of claim 1 further comprising a device for extracting the fluid from a formation surrounding a wellbore.

6. The apparatus of claim 5, wherein the light source, transparent member, detector and the device for extracting the fluid are part of a downhole tool.

7. The apparatus of claim 6, wherein the downhole tool is one of:
   a wireline tool; and a drilling tool.

8. The apparatus of claim 1, wherein the controller further determines a property of the fluid from the refractive index.

9. The apparatus of claim 8, wherein the property of the fluid is selected from a group consisting of: presence of an asphaltene; presence of bubbles; presence of crude oil; presence of water; and presence of a combination thereof.

10. The apparatus of claim 1, wherein the first detector comprises an array of sensing elements and wherein the controller determines a location of a center of the light received by the detector using interpolation between adjacent sensing elements and determines the refractive angle therefrom.

11. The apparatus of claim 1, wherein the first detector is selected from a group consisting of: a position sensitive detector array encapsulated in a clear material and immersed in the fluid; and a photo detector array encapsulated in a transparent material and immersed in the fluid.

12. The apparatus of claim 1 further comprising an aperture between the angular section and the planar surface of the second side.

13. The apparatus of claim 1, wherein the light source is selected from a group consisting of: a white light source, a wideband filtered white light source that covers the wavelength range of a suitable detector array, a super luminescent diode, a light emitting diode and a laser.

14. The apparatus of claim 1, wherein a refractive index of the transparent member and the selected angle are selected to provide at least a 25 degree spread for the refractive angle corresponding to fluids having a refractive index between 1.0 and 1.6.

15. The apparatus of claim 1, wherein the transparent member has a refractive index greater than 1.3 and the selected angle is greater than 30 degrees.

16. The apparatus of claim 1, wherein the transparent member has a refractive index of about 1.47 and an angle of the angled face with respect to an axis of the transparent member of about 42 degrees.

17. The apparatus of claim 1, wherein a desired refractive index resolution at the detector includes an angular spread in a beam output at the angled surface of the transparent member.

18. The apparatus of claim 1, wherein the angular spread in the beam output at the angled surface is approximately 50 degrees and the detector detects the light beam over a range of the angular spread.

19. The apparatus of claim 1, wherein the refractive index of the transparent member is 1.473.

20. The apparatus of claim 1, wherein the selected angle is about 42.7 degrees.

21. A method of determining a property of interest of a downhole fluid, comprising:
   providing the downhole fluid in a chamber;
   enclosing a transparent member in the chamber, the transparent member having a first side having a planar surface, a second side having a planar surface parallel to the first side and an angular section with an angled surface at a selected angle to the planar surface of the first side, wherein the angled surface and the parallel surface of the second side are in contact with the downhole fluid;
   passing light from a light source at the first side of the transparent member into the transparent member and from the transparent member into the downhole fluid in the chamber at the angled face, wherein the light passes into the downhole fluid at a refractive angle;
   receiving light passing through the downhole fluid at a first detector;
   determining the refractive angle from the light received at the first detector;
   determining, at a second detector, a reflective angle of light from the light source reflected from the planar surface of the second side; and
   determining a refractive index of the downhole fluid from at least one of the refractive angle and the reflective angle.

22. The method of claim 21 further comprising determining the property of interest of the fluid from the determined refractive index of the fluid.

23. The method of claim 21 further comprising:
   determining a refractive index of the fluid from light reflected by the fluid at the planar surface of the second side; and
   comparing the refractive index determined from the light passing through the fluid and the refractive index determined from the light reflected by the fluid to determine accuracy of one of the refractive indices.

24. The method of claim 21, wherein a wavelength of the light is selected from a group consisting of: a wavelength at which absorbance from asphaltene and absorbance from crude oil are below selected thresholds; 1100 nm; 1300 nm; 1400 nm; 1600 nm; a wavelength above 1600 nm; and a wavelength below 1000 nm.

* * * * *